United States Patent
Coghill

(10) Patent No.: US 7,213,475 B2
(45) Date of Patent: May 8, 2007

(54) MEASUREMENTS OF PARTICLE SIZE IN PNEUMATIC FLOWS

(75) Inventor: Peter John Coghill, Bexley (AU)

(73) Assignee: Common Wealth Scientific and Industrial Research Organisation, Campbel, Australian Capital Territory (AU)

( * ) Notice: Subject to any disclaimer, the term of this patent is extended or adjusted under 35 U.S.C. 154(b) by 8 days.

(21) Appl. No.: 10/312,327

(22) PCT Filed: Jun. 26, 2001

(86) PCT No.: PCT/AU01/00754

§ 371 (c)(1),
(2), (4) Date: Oct. 6, 2003

(87) PCT Pub. No.: WO02/01188

PCT Pub. Date: Jan. 3, 2002

(65) Prior Publication Data

US 2004/0045378 A1 Mar. 11, 2004

(30) Foreign Application Priority Data

Jun. 28, 2000 (AU) .................................. PQ8415

(51) Int. Cl.
*G01N 15/00* (2006.01)
(52) U.S. Cl. ..................................... 73/865.5
(58) Field of Classification Search ............... 73/865.5, 73/649, 61.75, 61.71
See application file for complete search history.

(56) References Cited

U.S. PATENT DOCUMENTS

| 3,805,591 | A | * | 4/1974 | Willis et al. ............... 73/24.03 |
| 3,919,050 | A | * | 11/1975 | Curby .......................... 435/39 |
| 4,073,193 | A | * | 2/1978 | Mastandrea ................ 73/865.5 |
| 4,212,190 | A | | 7/1980 | Coover et al. ............. 73/24.03 |
| 4,676,092 | A | | 6/1987 | Tuttle ........................... 73/38 |

FOREIGN PATENT DOCUMENTS

| GB | 2 241 783 A | | 9/1991 |
| JP | 63229334 A | * | 9/1988 |

* cited by examiner

*Primary Examiner*—Hezron Williams
*Assistant Examiner*—Tamiko Bellamy
(74) *Attorney, Agent, or Firm*—Sughrue Mion, PLLC

(57) ABSTRACT

This invention concerns the measurement of particle size of particles entrained in a gas. The apparatus (5) includes an acoustic sensor (10) used to monitor the acoustic signals produced by collisions of pneumatically conveyed particles with the sensor (10). Signal processing electronics and software (15) are used to determine, for each impact, the peak height of the acoustic signal. The particle size is calculated from the peak height distribution and either the signal (pulse) duration distribution or the airstream (impact) velocity, according to Hertzian Impact Theory.

17 Claims, 9 Drawing Sheets

MEASUREMENTS OF PARTICLE SIZE IN PNEUMATIC FLOWS

This application is a 371 of PCT/AU01/00754, filed Jun. 26, 2001; the disclosure of which is incorporated herein by reference.

TECHNICAL FIELD

This invention concerns the measurement of particle size, in particular the size of particles that are entrained in a gas. In a first aspect it concerns apparatus for making the measurements and in another aspect it concerns a measuring method.

BACKGROUND ART

Dry grinding processes are used in many industries, in particular coal-fired power generation and cement manufacture. In a coal-fired power station coal is pulverised then pneumatically conveyed to the boiler, for cement manufacture the ground meal is pneumatically conveyed to a kiln. For both cases oversize particles in the streams do not undergo a complete reaction. Measurement of the particle size in the feed is the first step to control of the grinding process. To date this has been done by sub-sampling of the pneumatic transport stream.

SUMMARY OF THE INVENTION

In a first aspect, the invention is an apparatus for measuring particle size in pneumatic flows, comprising:

An acoustic sensor to monitor the acoustic signals produced by collisions of pneumatically conveyed particles with the sensor. And, Signal processing electronics and software provided to determine, in respect of each impact, the peak height of the acoustic signal, to determine a peak height distribution from a series of acoustic signals, and then using either the pulse duration distribution or the air stream (impact) velocity, to calculate the particle size according to Hertzian Impact Theory.

The peak height distribution may be calculated in a first channel of a multi-channel analyser. The signal (pulse) duration distribution may be calculated from the series of acoustic signals (pulses) in a second channel of the same multi-channel analyser at the same time.

The air stream velocity may be measured using seperate equipment.

To measure the high frequency pulses coming in rapid succession, of potentially 100's of thousands a second, a specially designed acoustic sensor may be provided. The sensor has a large frequency bandwidth, to pick the signal up accurately, and is very well damped so as not to ring under continuous excitation. A thin co-polymer layer of polyvinyline difluride PVdF, a piezoelectric polymer, may be chosen for this application. PVdF is typically manufactured in layer thicknesses down to 10 microns and can be embedded in a polymeric material, preferably an abrasion resistant medium, such as polyurethane. Other materials may be used, but they should have nearly matching acoustic impedance so that the sound wave will pass through with little reverberation. The polymeric material may be of cylindrical shape and may have a curved base in order to eliminate the occurrence of end reflections. The PVdF material is preferably chosen to be resistant to operating up to temperatures of between about 75° C. and 125° C., and more preferably up to about 100° C.

To reduce the number of impacts to be measured at high industrial loadings it is desirable to reduce the area of transducer exposed to the substance. Therefore, a mask may be provided over the sensor to reduce the area of the piezoelectric polymer exposed to the substance. The mask may consist of a cap with a hole in the top. The cap is preferably of a metallic material. The cap may be screwed down over the sensor. The hole in the top of the cap preferably has a diameter of between about 1 mm and about 3 mm, and more preferably about 2 mm.

In a further embodiment, the head of the sensor may be tapered so as to reduce the number of impacts. In this embodiment, a mask may be used in addition to tapering the head in order to protect the barrel of the sensor.

With a properly designed sensor each impact produces a pulse, the duration and size of which conveys information about the particle size and velocity. The largest particles present in the powder should produce the signals of greatest amplitude. This allows a very natural method for examining the largest part of the particle size distribution accurately and therefore providing the information needed to improve grinding control.

The acoustic pulses produced by collisions are typically of sub-microsecond duration and can occur very frequently. Therefore the signals from the PVdF must be processed in an appropriate way to determine the peak height. The process of turning short duration spikes into reliable peak height information rapidly has been found to be similar to the problems encountered in processing data from photomultipliers in nuclear gauges. Nuclear electronics can therefore be selected to process the acoustic data from the PVdF layer.

The technique measures the peak compression from particle impacts so it is particularly well adapted to measure the coarser fractions of the particle size distribution, which have the largest signals. Monitoring coarse fractions of powder distributions is essential for control of dry grinding processes such as those used in the cement and coal industries. The technique could also be used to locate high solids concentration zones (ropes) in dust conveying pipes or ducts. Furthermore, in the construction of particle board, wood is typically shredded and blown into a compaction unit. Therefore, the technique may be used to determine the quantity of coarse wood particles incorporated into the board.

In a preferred embodiment, the apparatus includes an arm, to support the acoustic sensor, a pre-amplifier within the arm, and processing electronics typically containing a pulse shaping circuit and a multi-channel analyser. The arm is preferably metal to electrically shield the sensor from any outside interference. The barrel portion of the sensor sits in a mounting piece. Preferably, the arm passes through the mounting piece which allows the barrel of the sensor to be aligned at either about 0°, about 22° or about 45° to the air flow.

When a pneumatically conveyed particle strikes a surface, acoustic waves are launched into the material. By measuring these signals it is possible to determine information about the particle's size and velocity. In the simplest view of an elastic collision between a sphere and a plane the force imparted by the impact over its duration is equal to the change in momentum of the particle. For particles of a given density the acoustic signal is therefore related to the mass of the particle and hence the cube of the particle size.

The details of an elastic collision between a sphere and a plane have been worked out and go under the name of Hertzian Impact Theory [Buttle and Scruby 1989]. The results may be summarised in two equations one for the peak compressional force, F, of the impact and the other for the duration, D.

$$F = f(E, \nu, \rho) V^{6/5} R^2 \quad (1)$$

$$D = d(E, \nu, \rho) V^{-1/5} R \quad (2)$$

where V is the impact velocity, R is the particle radius, and f(E, ν, π), and d(E, ν, σ) are functions of the material co-efficients, E is the Young's Modulus, ν the Poisson Ratio and ρ the density. Notice that the product of F and D is proportional to $VR^3$ and hence the momentum.

In principle, from measuring the pulse height, which is related to peak compression, and the pulse duration it is possible to retrieve the particle size and velocity of the particle. The duration measurement is however difficult to achieve so that it may well be simplest to measure the peak compression using the apparatus, and the flow velocity in the air stream by a separate technique. The impact times for sub-millimetre particles are typically shorter than a few microseconds. For instance using the material properties of glass, a velocity of 20 m/s and a particle size of 100 microns the impact duration is approximately 0.2 microseconds. This short duration allows the measurement of many tens of thousands of impacts a second giving a statistically significant data set rapidly.

The duration of an impact may be recorded by transforming the time an impact is above a threshold value into a peak height signal electronically. The peak height would then be recorded on a multi-channel analyser.

An advantage of the present invention is that the apparatus has shown the capacity to measure particle diameters down to about 50 μm, operate at loadings of about 0.5 kgm$^{-3}$ and at temperatures of about 100° C. A further advantage is that the apparatus has shown the capacity to discriminate between powders with about a 1% difference in peak size for samples at about 150 μm.

The apparatus may include a velocity device to measure the flow velocity in the airstream. The device may use ultrasonic Doppler technique to measure velocity. This technique is advantageous for mobile impact size monitors. The technique measures the reflections from a pulse off particles and turbulence. The flow velocity is determined by the Doppler shift in frequency between the transmitted pulse and the reflections. Alternatively, the impact size monitor may be installed on site for long term operation. The device may in such instances be a pressure probe, pitot tube, hot wire anemometer, or may determine velocity by mean of laser Doppler velocimetry or particle image velocimetry. Furthermore, techniques to measure flow such as an ultrasonic transit time measurement or a pressure differential could be used.

In a further aspect, the invention is a method of measuring particle size in pneumatic flows. The method includes the following steps:

Monitoring the acoustic signals produced by collisions of pneumatically transported particles with the sensor.

Determining, in respect of each impact, the peak height of the acoustic signal.

Determining a peak height distribution from a series of acoustic signals. Then,

Calculating, using either the pulse duration distribution or the air stream (impact) velocity, the particle size according to Hertzian Impact Theory.

BRIEF DESCRIPTION OF THE DRAWINGS

An example of the invention will now be described with reference to the accompanying drawings, in which.

BEST MODES OF THE INVENTION

The following description is divided into sections that examine the apparatus design, the numerical simulations, and experimental laboratory results on the apparatus. The laboratory experiments were carried out to determine the feasibility of using the apparatus in an industrial environment. The experiments included testing the effect of different particle loadings, sensor temperature sensitivity, particle distribution across the width of the particle transport pipe and the effects of excessive wear.

1. Apparatus Design

Figure 1:
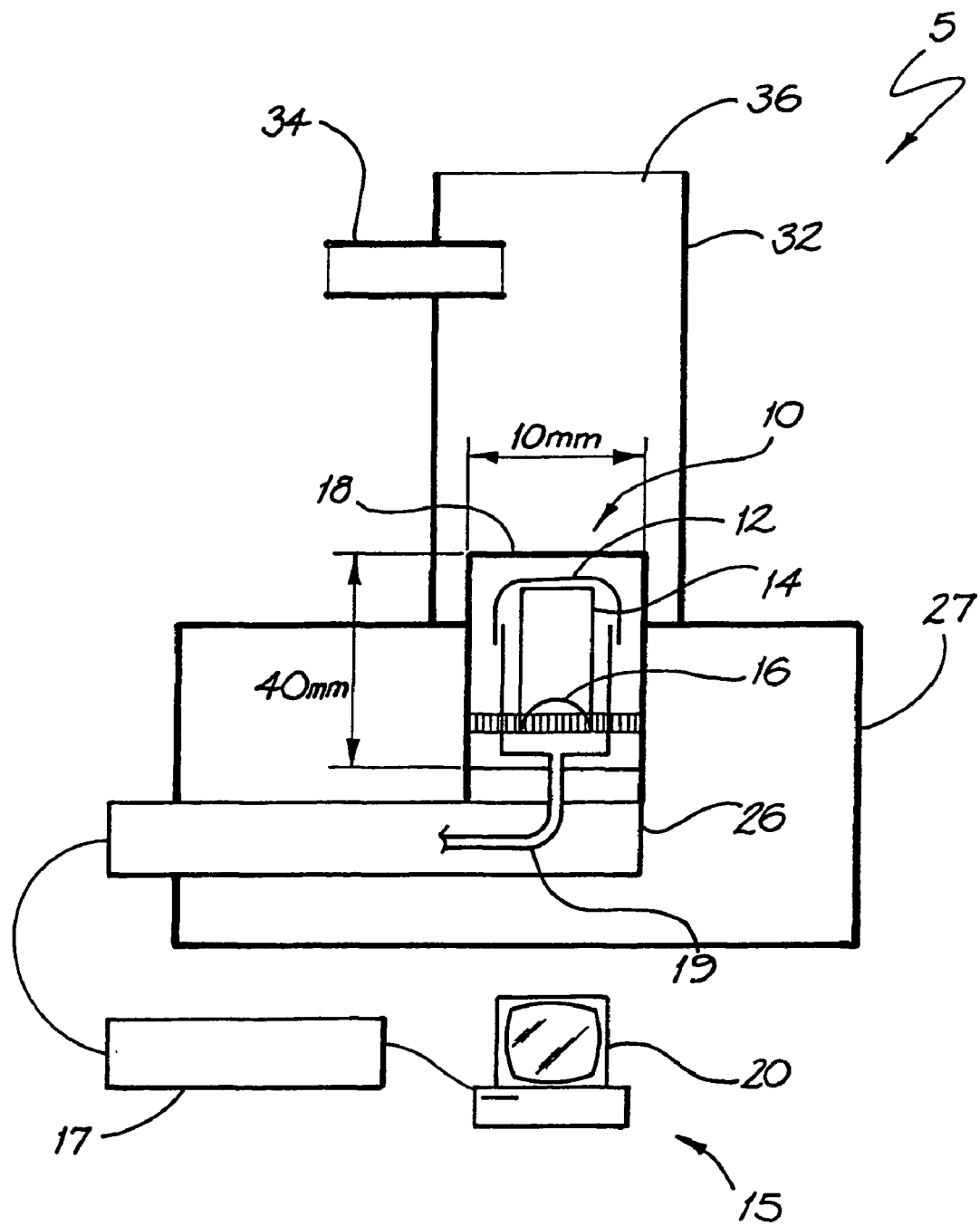
FIG. 1 is a schematic diagram of an apparatus for measuring particle size in an industrial process.

In FIG. 1, the apparatus 5 includes an acoustic sensor indicated generally at 10, and signal processing electronics and software, indicated generally at 15.

The acoustic sensor 10 consists of a PVdF layer 12 sandwiched between an inner epoxy block 14 and an outer epoxy encasing 18. The inner epoxy bloc, 14 and the outer epoxy encasing 18 are matched so that the occurrence of internal reflections of ultrasound are reduced to about zero. End reflections are eliminated by curving the base 16 of the epoxy block 14 and through the natural absorption of the epoxy which attenuates ultrasound at approximately 10 dB/cm. The impact sensor 10 has a total length of 40 mm and a diameter of 10 mm. The PVdF layer 12 has an area of 25 mm$^2$. A coaxial cable 19 is connected to the PVdF layer 12.

The sensor 10 is constructed with either 25 micron PVdF or 100 micron PVdF copolymer layers. In both cases the copolymer is resistant to operating at high temperatures (up to 100° C.). This is an important consideration for industrial deployment of the sensor as 70° C. temperatures are common in pneumatic transport systems in black-coal fired power stations.

In a further embodiment a mask (not shown) can be employed to cover the upper face and sides of the sensor 10.

The compressive force produced by an impact is distributed over the cross-sectional area of the sensor to produce an output voltage. Miniaturising the active area offers great gains in sensitivity. Furthermore, fringing collisions may produce partial signals compared to those when the particle strikes near the centre of the PVdF element. Therefore, the mask acts to ensure that the particles strike above the central region of the sensor 10. The mask consists of a metal cap with a 2 mm diameter hole in the top, and the mask is screwed down over the transducer. At high loadings of powder the mask was shown to be useful in reducing the active area of the sensor 10. Alternatively, to achieve the same effect the front face of the sensor 10 may be tapered. To achieve sensors which taper to a 2 mm diameter circle, a total front face thickness of 9 mm was required. A mask may still be used to protect the sides of the sensor.

The sensor is positioned in a mounting piece 27. The apparatus 5 includes an arm 26, which houses a pre-amplifier. The arm 26 is metal to electrically shield the sensor from any outside interference. One end of the arm 26 passes through the mounting piece 27 that enables the sensor 10 to be aligned between 0° and 45° to the flow of the airstream.

A pneumatic transport perspex pipe 32 is mounted over the sensor. The pipe 32 has a diameter of 40 mm. In use, compressed air is fed through an inlet 34 and angled down the pipe 32 at variable pressure to create an air stream of controlled velocity of 21.3 m/s. Particles are introduced at the top of the pipe 32 by means of a feeder at 36. The pneumatically conveyed particles impact the sensor 10.

The impacts of particles on the sensor 10 produce voltage spikes of approximately 0.4 µs in duration, which occur against a background of low frequency fluctuations due to pressure variations or turbulence in the airflow.

The processing electronics contains in sequence, a pre-amplifier and high pass filter to remove the low frequency background, a pulse shaping amplifier card and a multi-channel analyser (MCA) 17. The MCA 17 records the peak height spectrum of the impact pulses, which can be related to the particle size distribution in the pneumatic transport stream. The MCA 17 is connected to a PC 20.

Figure 2A:
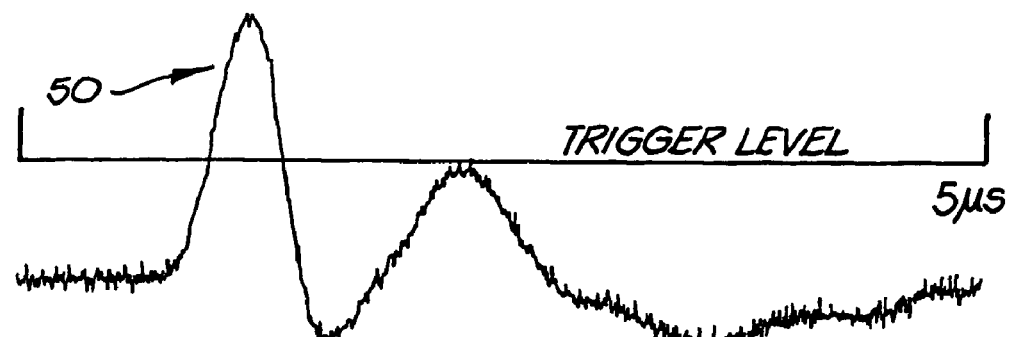
FIG. 2a is a diagram of a typical pulse from a preamplifier of the apparatus of FIG. 1.
Figure 2B:
FIG. 2b is a diagram of the pulse of FIG. 2a modified by grounding the signal 1.5 microseconds after triggering for 10 microseconds.
Figure 2C:
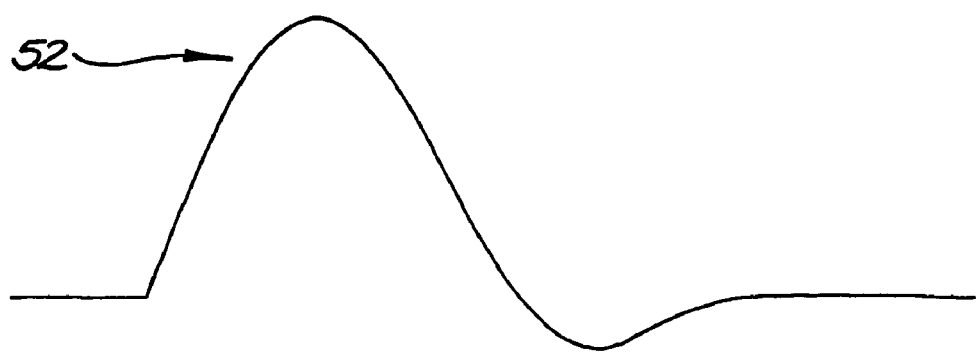
FIG. 2c is a diagram of the pulse of FIG. 2a after shaping performed by a shaping amplifier prior to input to a multi channel analyser.

The pre-amplifier has a gain of ten and a RC high pass filter to reduce the low frequency noise due to air turbulence. The pulse shaping amplifier card is designed to condition the signal from the pre-amplifier for processing by the MCA 17. The card involved two stages. The first stage includes a second high pass filter and amplification means. The second high pass filter has a much sharper roll off than the initial filter stage in the pre-amplifier. The pulse is modified by this processing as shown in FIG. 2. FIG. 2a illustrates a typical pulse 50 from the preamplifier. FIG. 2b illustrates the pulse 51 modified by grounding the signal 1.5 µs after triggering for 10 µs. FIG. 2c illustrates the resulting pulse 52 after pulse shaping prior to input of the MCA 17. The purpose of this two stage process is to allow the shaping part of the circuit access to a single pulse and a flat baseline to produce an undisturbed output whose pulse width is several microseconds 2. Fluid Dynamic Modelling Experiment and Results Fluid Dynamic modelling of the apparatus was undertaken independently to determine the size range of particles which could be monitored by the sensor and the effect of sensor geometry on that size range. In this simulation 31,250 particles were "introduced" into an air flow of 30 m/s, for each of nine size ranges between 4 and 200 microns. The particles were released randomly over a 44 mm radius circle above the apparatus 5. The simulation was repeated for two different particle specific gravities of 0.9 gm/cc and 2.5 gm/cc.

FIG. 3 illustrates the four sensor geometries that were used. Geometries a and b are flat transducers while cases c and d use tapered faces. The flat and tapered transducers were each modelled at 0° and 45° to the flow. For each case the number of particle impacts on the 2 mm square sensitive area at the centre of the face and the total particle velocity at impact were recorded.

Figure 3A:
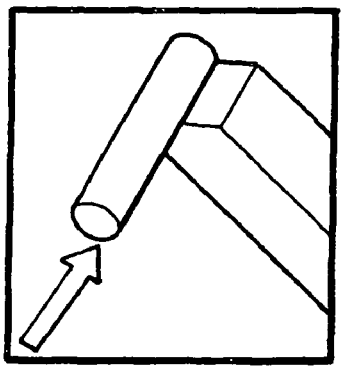
FIGS. 3a, 3b, 3c and 3d illustrate four sensor geometries and their orientations relative to the flow.
Figure 3B:
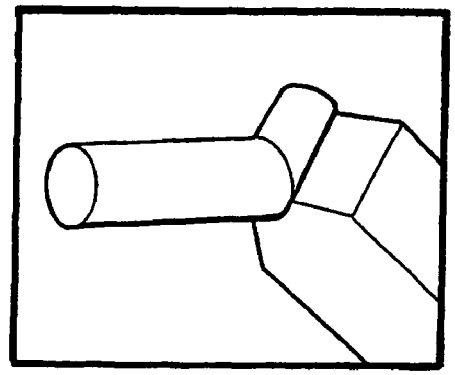
Figure 3C:
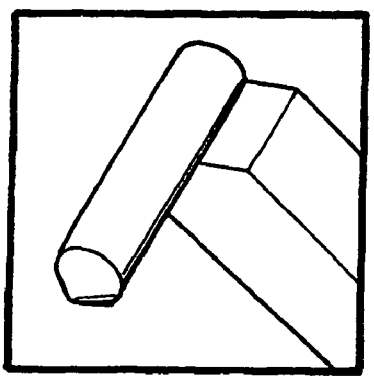
Figure 4A:
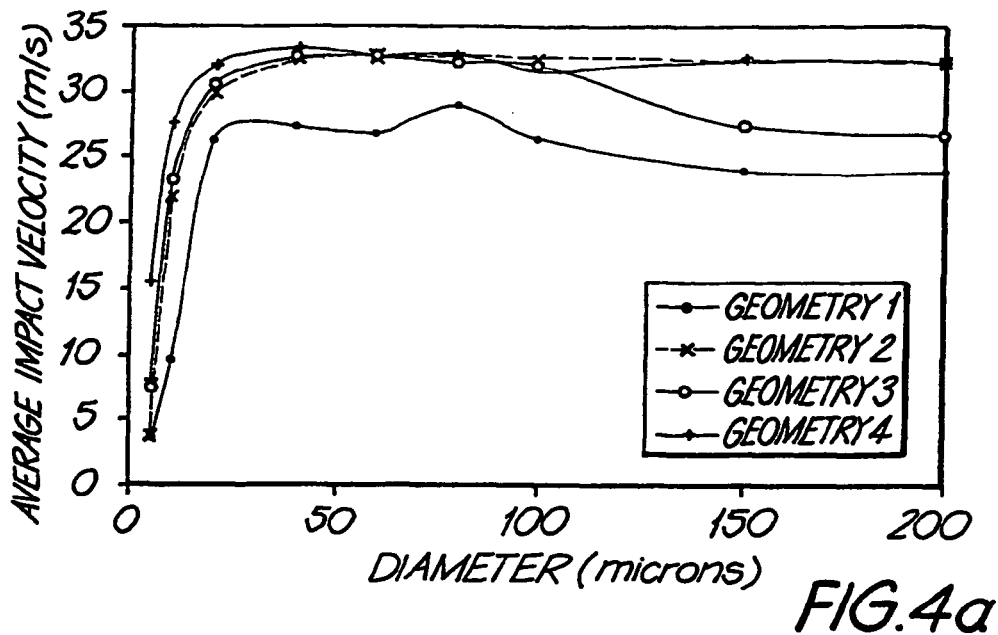
FIG. 4a is a graph showing the number of particle impacts, as a function of diameter.
Figure 4B:
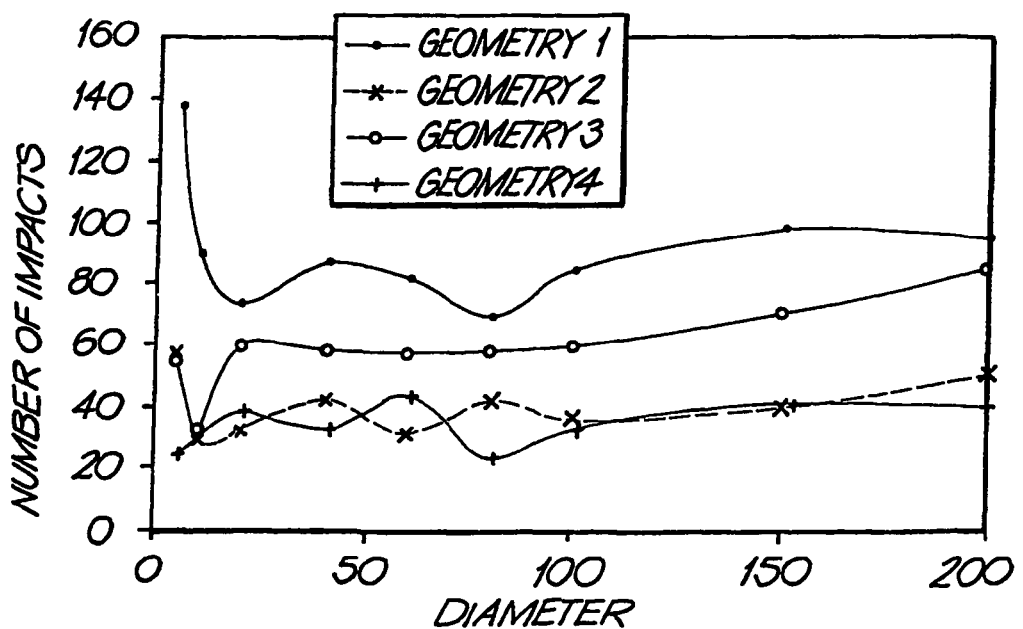
FIG. 4b is a graph showing the average impact velocities, as a function of diameter.
Figure 5A:
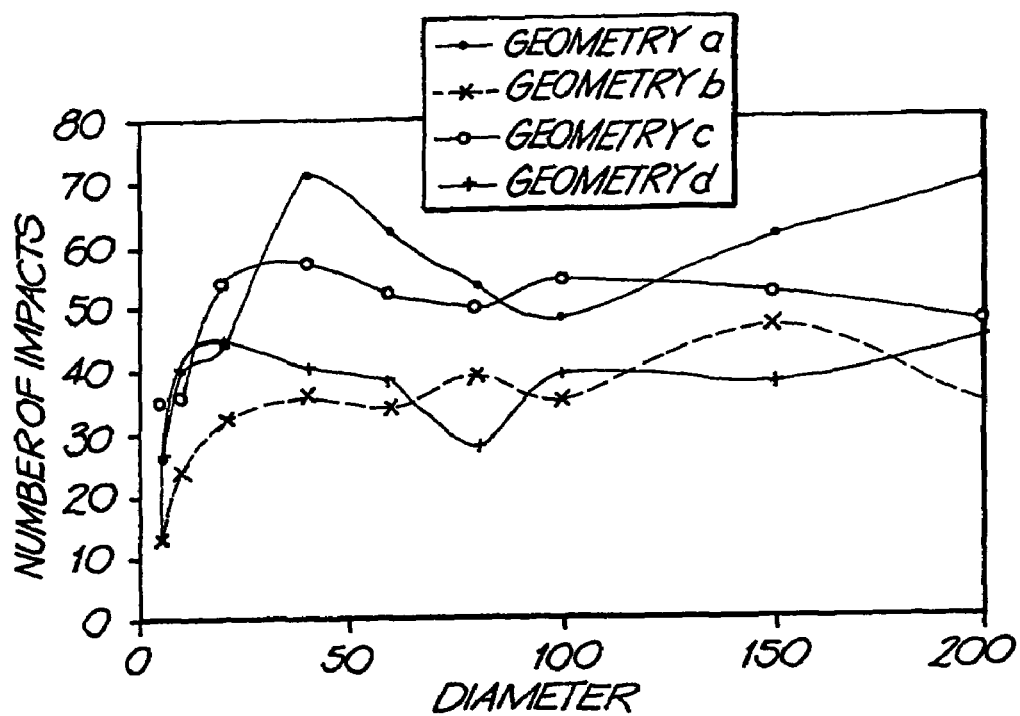
FIG. 5a is a graph showing the number of particle impacts, as a function of diameter, onto the sensor geometries shown in FIG. 3, without particle bouncing.
Figure 5B:
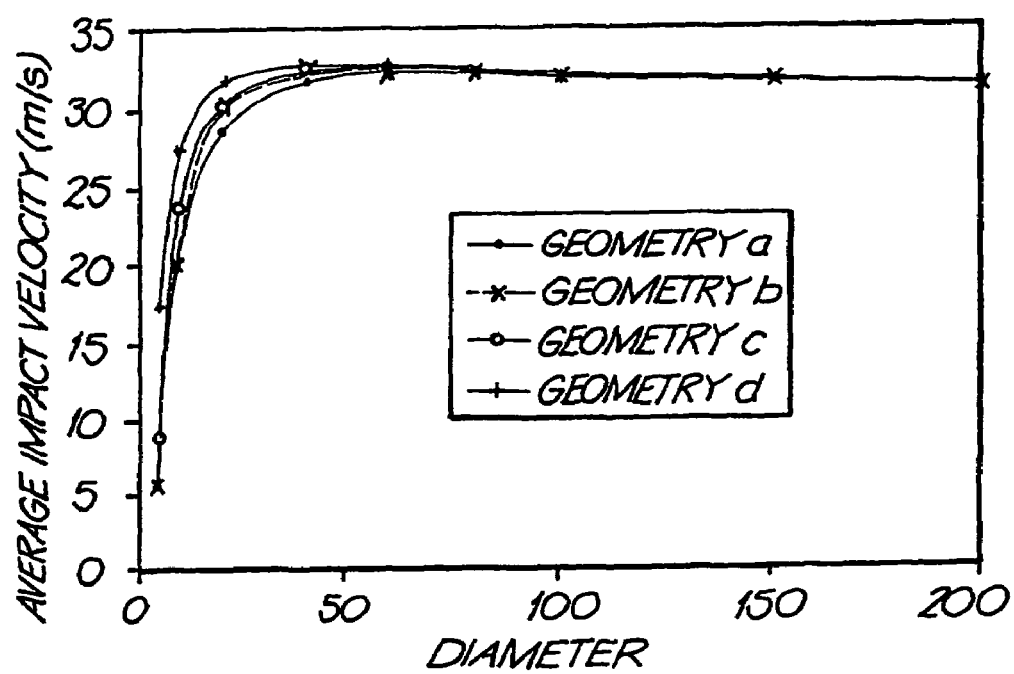
FIG. 5b is a graph showing the average impact velocities, as a function of diameter, onto the sensor geometries shown in FIG. 3 without particle bouncing.

FIGS. 4a and 4b have two prominent features. First, the drop in impact velocity below 50 microns and secondly the difference between geometry 'a' and the other geometries. Geometry 'a', where the frontface of a flat sensor is at 90° to the flow as shown in FIG. 3a, departs from the results of the angled cases in terms of the number of impacts and their velocity. This is caused by the particles striking the sensor and then bouncing and hitting the sensitive area. In FIGS. 5a and 5b the bounce effect is removed by changing the coefficient of restitution to zero for the sensor, so that if a particle hits the sensor it sticks. In FIG. 5 the velocity at impacts results largely correspond in all four cases.

The results shown in FIGS. 4 and 5 are illustrative of particles with a specific gravity of 2.5 gm/cc. Changing the particle density to 0.9 gm/cc had only a marginal effect on the results.

Two important practical conclusions can be drawn from the simulations. First, the apparatus 5 should be able to measure accurately particles down to approximately 50 microns before the impact velocity is disturbed by airflow effects. Particles less than 50 microns are entrained in the air-flow and either do not strike the sensitive area or hit only glancing blows. Second, angled sensors should be used to avoid problems with bouncing particles.

3. Experimental Results

Figure 3D:
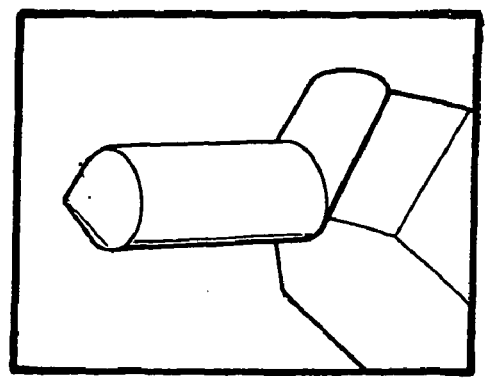

Compressed air was blown down a perspex tube onto the impact sensor at a velocity of 21.3 ms$^{-1}$. For all experiments, unless otherwise stated, the probe used was inclined at 45 degrees to the air flow and tapered as shown in FIG. 3d. A mask with a 2 mm diameter hole was used to cover the transducer.

Figure 6:
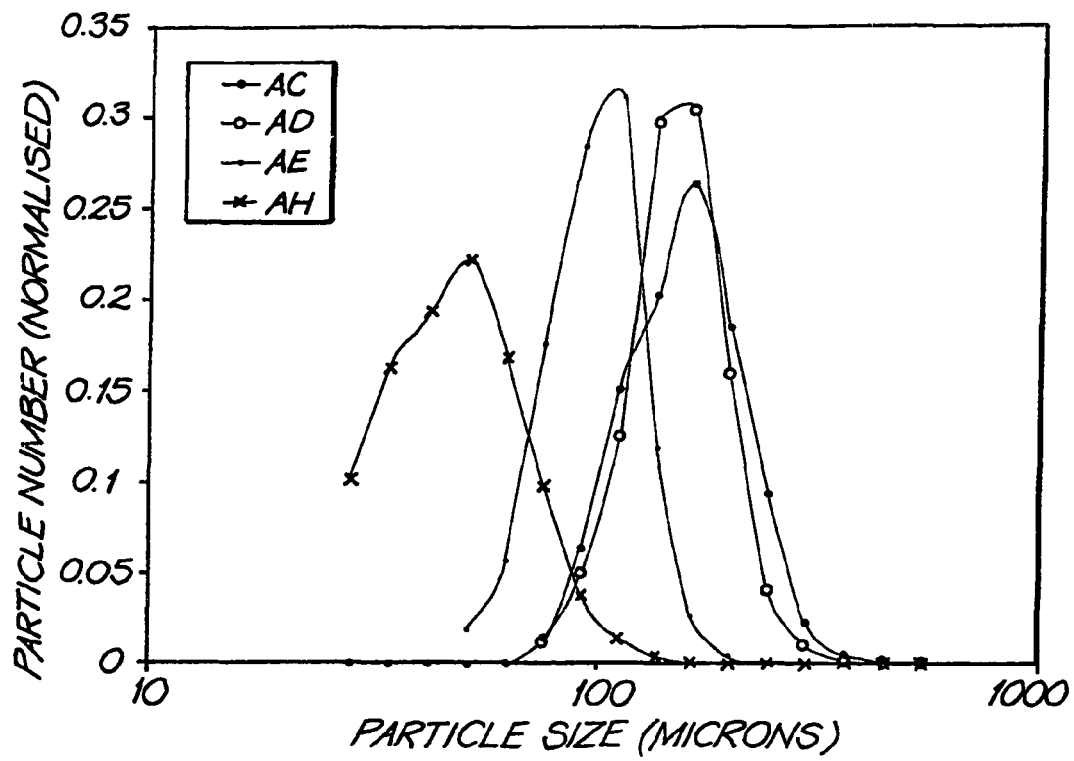
FIG. 6 is a graph showing the normalised particle size distribution of the four grades of ballotini used in the experiments.

The powders used in these experiments were four grades of glass ballotini. As the probe counts individual particles, the apparatus 30 output is related to the number rather than the more standard volume distribution of the particles. Instead of d50, the most numerous or peak size will be used to indicate the relation between the four grades. The number size distributions of these 4 grades are shown in FIG. 6 and the peak positions given in Table 1. AE dust is roughly equivalent in size and density to raw cement meal, while AH dust is a reasonable size model of pulverised coal. In all experiments, 40 grams of powder was released into the Perspex tube 32.

Figure 7:
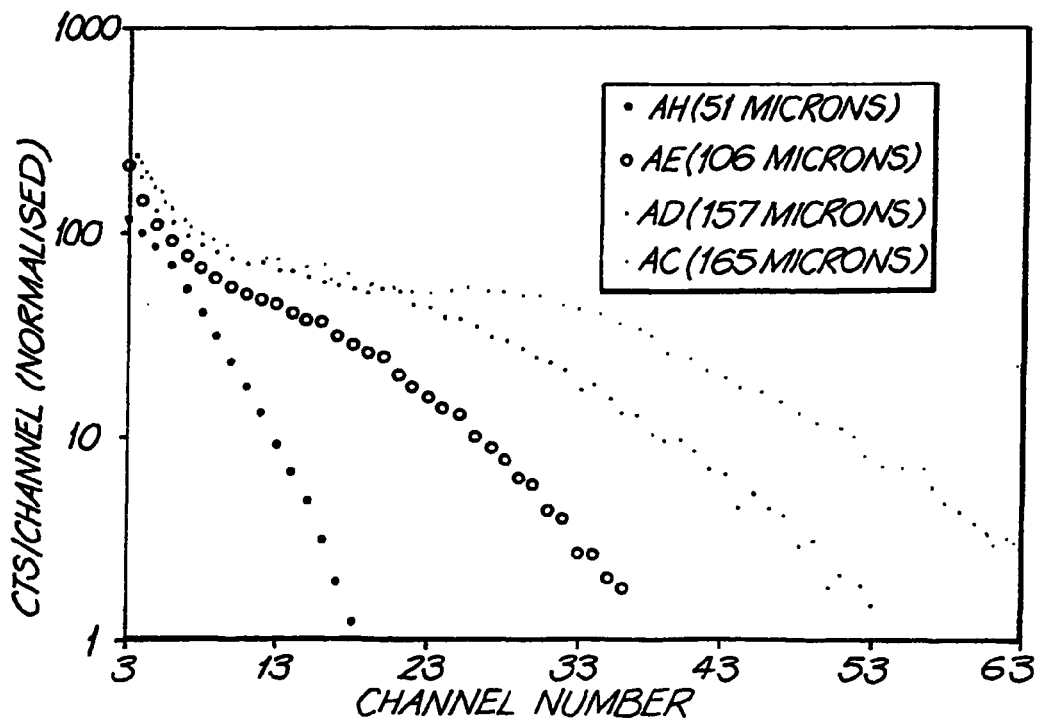
FIG. 7 is a graph showing pulse height spectra for the four grades of ballotini.

The peak height spectra for the four grades of ballotini is shown in FIG. 7, good discrimination is achieved between all grades, and is especially impressive for the coarsest grades (AC,AD) where the peak positions differ by only 8 microns. It can be estimated that a 1% difference in mean size could have been resolved for samples with peak positions around 150 μm. The spread of the spectra due to air turbulence and other baseline noise effects corresponds to approximately plus or minus one channel on FIG. 7.

Assuming the minimum size of measurable particle to be 50 microns a prediction for the total number of impacts recorded by the impact size monitor for a 40 gm sample of the four powders can be made. For each grade the average channel number or peak height can also be calculated. This is related to the mean size of the particles striking the sensor. The ratio of the average peak heights can be calculated from the particle size distribution and compared to experimental measurement. Table 1 shows these comparisons. The results are in reasonable agreement considering the conversion from volume to number distribution.

TABLE 1

Measured results compared to predictions from ballotini particle size distribution.

| Glass Grade | Peak Position (microns) | By Calculation | | Experiment | |
|---|---|---|---|---|---|
| | | No. of Hits | Av. Peak Ht. Ratio | No. of Hits | Av. Peak Ht. Ratio |
| AC | 165 | 22,000 | 1 | 34,300 | 1 |
| AD | 157 | 39,000 | 0.68 | 57,600 | 0.82 |
| AE | 106 | 84,000 | 0.41 | 111,800 | 0.61 |
| AH | 50 | 230,000 | 0.21 | 230,000 | 0.36 |

3a. Loading Effects on Peak Height Spectra

The rate of feed of powder into the apparatus was changed to determine whether it has an effect on the peak height spectra. Measurements were made initially at a mean powder loading of <0.02 kg m$^{-3}$ referred to as low loading. This was achieved by slowly feeding the dust into the apparatus. Measurements were then made at a powder loading of approximately 0.4 kg m$^{-3}$ for the three largest ballotini grades and approximately 0.6 kg m$^{-3}$ for AH ballotini, referred to as the high loading. The high loading is achieved by feeding the powder into the apparatus quickly using a funnel to provide a repeatable rate.

Figure 8:
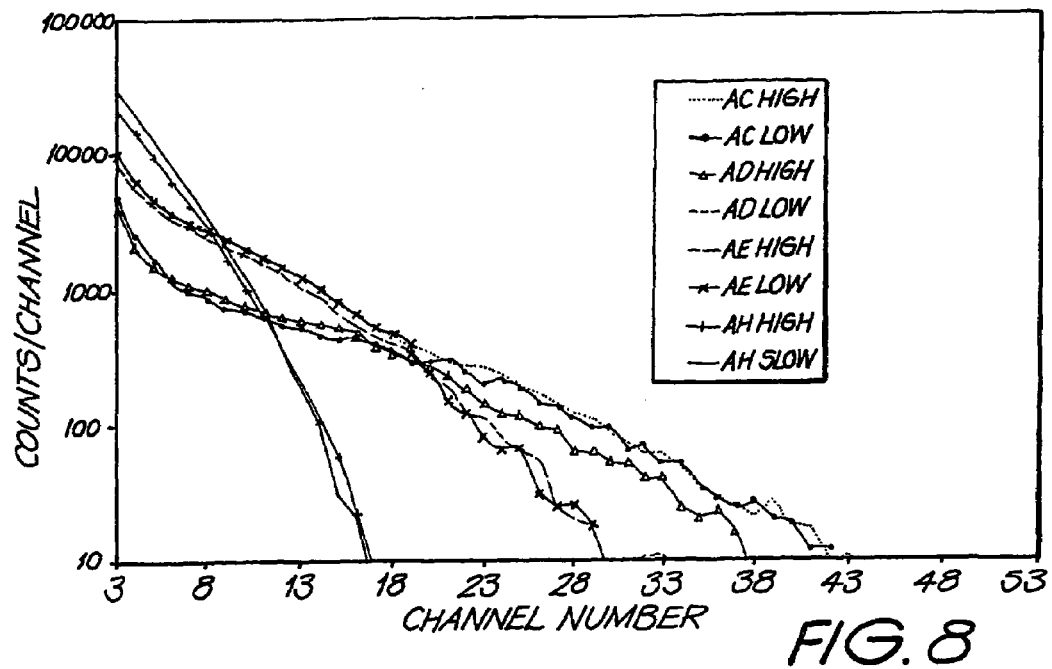
FIG. 8 is a graph showing the high and low loading measurements with the sensor at 45 degrees to the flow.
Figure 9:
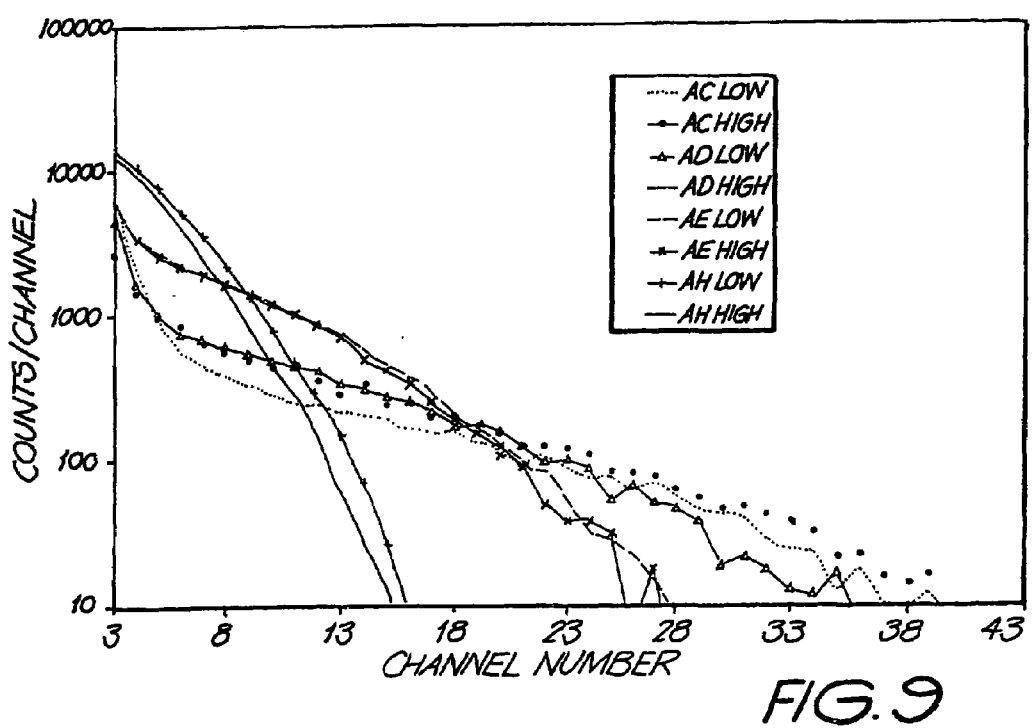
FIG. 9 is a graph showing the high and low loading measurements with the sensor parallel to the flow.

Peak height spectra were measured for all four grades with the sensor inclined at 45 degrees to the flow and at 0 degrees to the flow. The results of the ratio of average peak height between high and low flow are given for the two angles in Table 2. The spectra are shown in FIGS. 8 and 9.

TABLE 2

Ratio of the Average Peak Heights at high and low flow for the four grades of ballotini.

| Ballotini Grade | 0 degrees High/Low Av. Pk Hts. | 45 degrees High/Low Av. Pk Hts. |
|---|---|---|
| AC | 0.841 | 1.00 |
| AD | 0.907 | 1.02 |

TABLE 2-continued

Ratio of the Average Peak Heights at high and low flow for the four grades of ballotini.

| Ballotini Grade | 0 degrees High/Low Av. Pk Hts. | 45 degrees High/Low Av. Pk Hts. |
|---|---|---|
| AE | 0.974 | 1.00 |
| AH | 0.981 | 1.02 |

In the case of the 0 degree transducer, there is a decrease in average peak height as the flow is increased, whereas the 45-degree case remains unchanged. The most likely cause of the reduction is peak height is a crowding effect where particles collide with each other in the neighbourhood of the sensor face. This experiment demonstrates that it is possible to measure at flow rates in the range 0.4–0.6 kg m$^{-3}$ with the impact size monitor as long as the sensor is angled to the flow. This flow rate is typical of many industrial applications.

3b. The Effect of Temperature on ISM Sensitivity

As the temperature of the pneumatic flow streams in industry is often significantly higher than ambient (approximately 70° C. in black coal power stations) tests were made of the copolymer PVdF transducers at elevated temperatures. The transducers were heated for 1 hour and then the measurements performed immediately on withdrawal from the furnace. It was anticipated that the 4 mm front-face of epoxy was sufficient to retain the heat during the experiment. Table 3 below shows the average peak heights at four temperatures normalised to room temperature. A slight increase in sensitivity was observed at eighty degrees but no major changes were detected in the spectra.

TABLE 3

The average peak height measured for AD ballotini at four sensor temperatures normalised to room temperature result.

| Temperature (° C.) | Average Peak Ht (Channel No.) |
|---|---|
| 25 | 1.00 |
| 50 | 1.01 |
| 70 | 0.99 |
| 80 | 1.07 |

3c. Measurements Made in a Horizontal Re-circulating Rig.

The apparatus was tested next in a horizontal re-circulating flow rig in an attempt to measure that particle distribution across the pipe. The flow rig was constructed originally to model conditions of pneumatic transport in a coal-fired power station fuel duct The transport pipe in the flow rig was 300 mm in diameter and approximately 20 m in length, with the air being fan forced into circulation at velocities up to 35 m/s. Powder could be added via a feed valve and removed by an air cyclone which operated on a byline of the flow rig.

As the pipe was horizontal it was expected that the powder flow would be non-uniform across the pipe. Upon taking measurements in the pipe it was found that the amount and size of material suspended in the stream decreased steadily over the time frame of minutes. The loss of suspended particles is believed to be due to particles being caught in experimental ports and the fan casing. All the experiments reported in this section attempted to overcome these problems by rapid measurement and repeats after a certain fixed time being used to correct the data.

Figure 10:
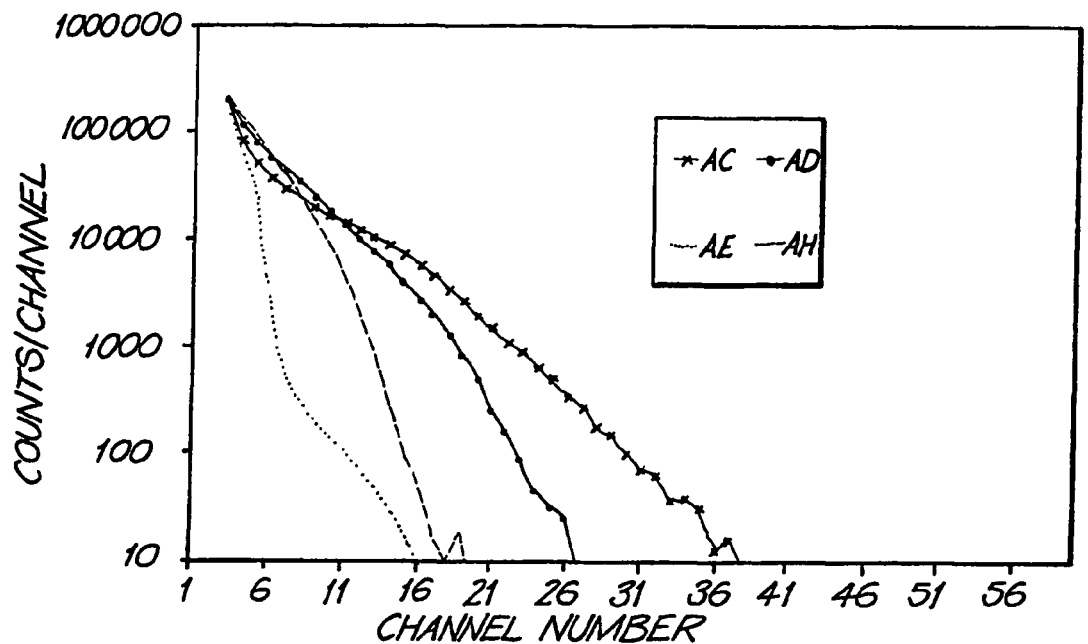
FIG. 10 is a graph showing the peak height spectra of the four ballotini grades as measured in a recirculating rig.

FIG. 10 shows the spectra recorded by the four grades of ballotini in the flow rig with a flow speed of 30 m/s and the probe located at the pipe centre. The different grades are still clearly distinguishable though the spectra show a marked increase in fine particles over those of the tests in the compressed air apparatus. The peak height spectra was measured at a number of positions in the pipe for a notional loading of 0.2 kg/m$^3$ of AE dust.

Figure 11:
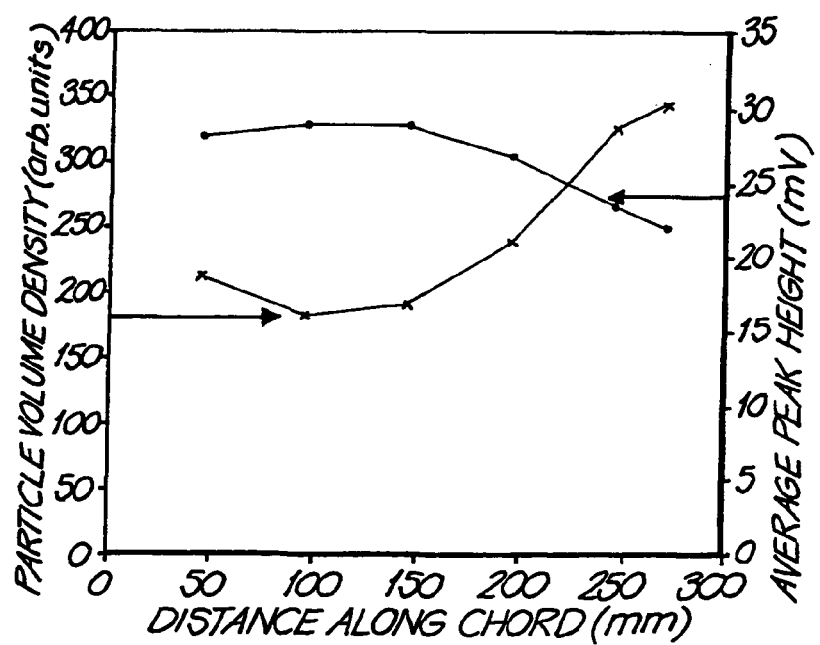
FIG. 11 is a graph showing the variation of particle density and average peak height across the flow rig for a grade (AE) of ballotini.

FIG. 11 plots the average peak height and the particle volume density across a pipe diameter inclined at 45 degrees to the vertical. The results indicate a lower particle velocity towards the bottom of the pipe and a greater number of particles towards the bottom of the pipe. The impact size monitor demonstrated its usefulness in diagnosing the state of particle flow in a pneumatic transport pipe.

3d. Wear and its Effect on Sensitivity

One of the major issues in deploying the apparatus in industrial flows is the amount of wear of the sensor due to particle abrasion. It is obviously desirable for the sensor to be able to withstand abrasion for as long as possible. To measure the rate at which wear is likely to occur a small rod of the epoxy used in transducer manufacture was exposed to pneumatic flow in the re-circulating flow rig for a period of eight hours. The amount of powder was constantly replenished to keep the solid loading between 0.5 and 1 kg/m$^{-3}$ at a velocity of 30 ms$^{-1}$. The rate of front face abrasion was 0.01 mm/(kg/m$^3$ hr). There was increased wear on the edges of the rod, suggesting that some protection for the sides of the sensors may be useful.

The other important issue in determining the lifetime of the sensor is the how quickly the sensitivity changes as the depth of the front-face epoxy layer is reduced.

Figure 12:
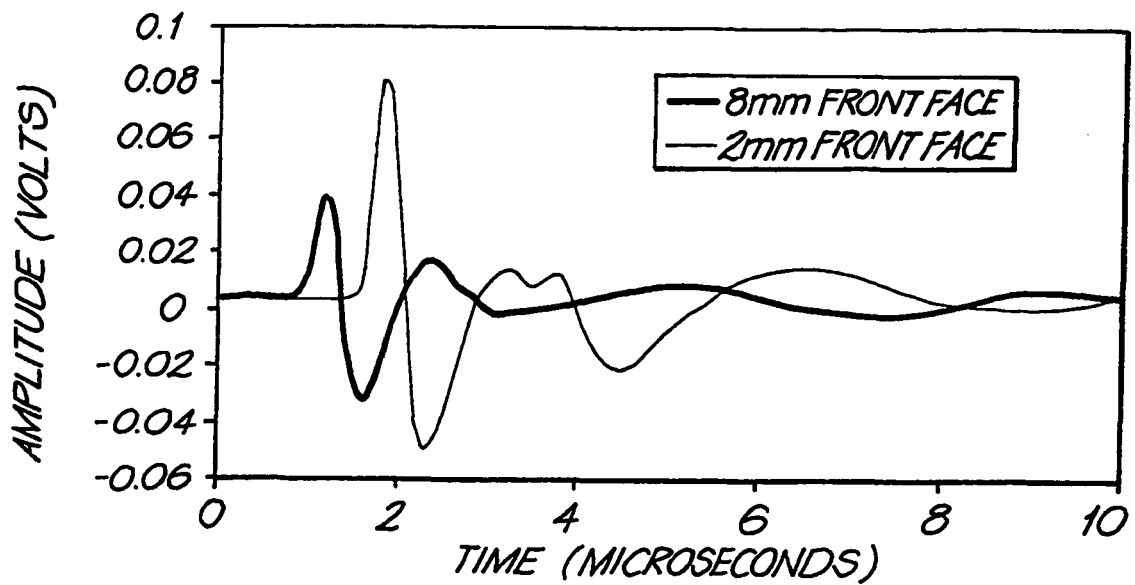
FIG. 12 is a graph showing the impact waveforms, averaged over 128 hits using AE ballotini, for sensors with an 8 mm and a 2 mm front face.

FIG. 12 shows two waveforms, the first is the average of 128 impacts on a transducer with a front-face thickness of 8 mm and the second is for a front-face thickness of 2 mm. In both cases AE grade ballotini was used. The sensor with the thinner front face showed a markedly greater peak height and hence sensitivity.

Figure 13:
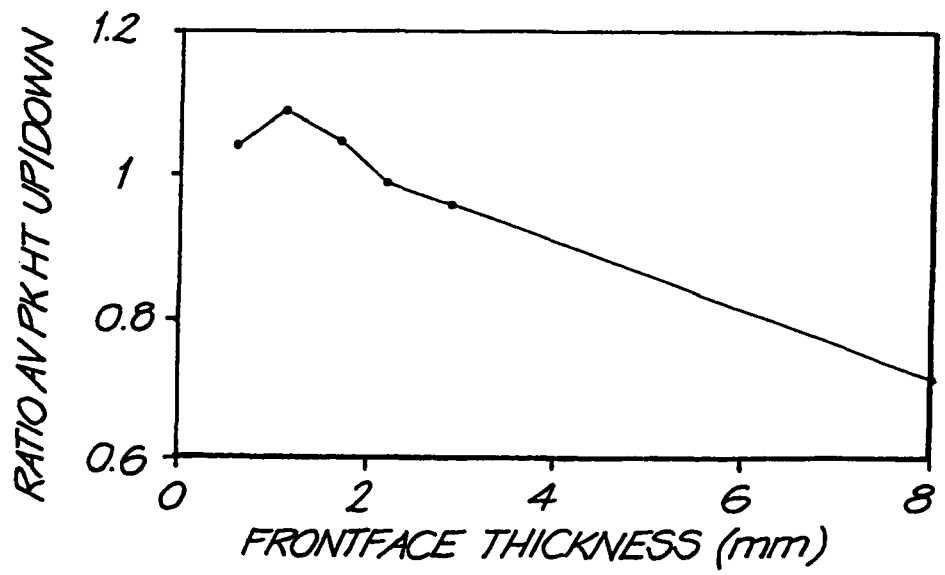
FIG. 13 is a graph showing the ratio of positive to negative average peak heights as a function of front-face depth.

It is interesting to note that the ratio of the height of the initial upward pike to that of the negative going overshoot changes with the front-face thickness. This suggests that the increase in sensitivity with wear could be allowed for by monitoring the ratio of the positive and negative going pulse peaks and inferring the overall sensitivity. FIG. 13 shows the ratio of positive to negative peaks at a variety of depths, the ratio behaves simply for depths greater than 2 mm and could be used to correct for sensitivity changes.

The experiments demonstrated the ability of the impact size monitor to discriminate between powders with a 1% difference in peak size. The impact size monitor operated at industrial loadings of 0.5 kg m$^{-3}$ of powder and measured particles down to 50 microns in size.

The impact size monitor tested in the experiments above demonstrated improved results when compared to a primitive impact size monitor discussed below. These improvements consisted of enhancing the acoustic match of the PVdF element to its surrounds, changing the size and shape of the PVdF element used by tapering the PVdF element or using a mask and improving the signal processing electronics.

In the primitive monitor, particles conveyed in a pneumatic air stream collided with a post that includes a PVdF layer. The post was designed both as an acoustic guide and also to dissipate the signal after it passes through the PVdF layer to prevent signal reflections. The PVdF layer was glued 4 mm below the surface of the post and was 110 microns thick The post material was aluminium, which is a reasonable acoustic match with the PVdF. The post had a diameter of 2.5 cm and the PVdF element was approximately 1 cm square. Tests as exemplified in the first embodiment sensor above were performed on this sensor.

In use, the signal from the PVdF was passed through a pre-amplifier and then into a high pass filter to remove low frequency noise generated by turbulence in the compressed air stream. The filter was a simple high pass RC circuit with a roll-over point of 150 kHz. After filtering, a peak detector and shaping circuit was used to present the signal to an A/D converter and thence to a multi-channel analyser which converted the digitised signals into a pulse height spectrum.

Return signals from a typical glass sphere impact typically included reflections from the front face of the transducer are present as trailing signals spaced at about 2 microseconds. It was shown that a minimum peak height of 10 mV was required to trigger the peak detect circuitry.

This initial test design is sub-optimal. At a airstream of 14 ms$^{-1}$ and a particle density of 2 gmcc$^{-1}$ particles of 100 microns or above were detected. Measurements were only able to be made at low particle loadings due ot the reverberation of the sensor. Analysis of pre-amplifier output, suggested that such a target of 50 microns would be achievable with improvements in the signal processing electronics and by enhancing the acoustic matching of the PVdF and the surrounds.

This has been achieved in the first embodiment

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An apparatus for measuring particle size in pneumatic flows, comprising:
    an acoustic sensor to monitor the acoustic signals produced by collisions of pneumatically conveyed particles with the sensor, wherein the acoustic sensor includes a co-polymer layer embedded in a polymeric material; and
    signal processing electronics and software provided to determine, in respect of each impact, the peak height of the acoustic signal, to determine a peak height distibution from a series of acoustic signals, and then to calculate the particle size according to Hertzian Impact Theory.

2. An apparatus according to claim 1, wherein the signal processing electronics includes a multi-channel analyser, and the peak height distribution is calculated in a first channel and a signal duration distribution is calculated from the series of acoustic signals in a second channel of the analyser.

3. An apparatus according to claim 1 wherein the acoustic impedances of the co-polymer and the polymeric material are substantially equal.

4. An apparatus according to claim 1 or 3, wherein the co-polymer layer is polyvinyline difluoride (PVdF).

5. An apparatus according to claim 1, wherein the polymeric material is in the form of a block and has a base which is shaped to eliminate end reflections.

6. An apparatus according to claim 4 wherein the co-polymer material is able to withstand operating temperatures of between about 50° C. and about 110° C.

7. An apparatus according to claim 6 wherein the co-polymer material is able to withstand operating temperatures of up to about 80° C.

8. An apparatus according to claim 1, wherein the sensor has a head which is tapered to reduce the surface area.

9. An apparatus according to claim 1, wherein the signal processing electronics are based on nuclear gauge electronics.

10. An apparatus according to claim 9, where the electronics includes
    a pre-amplifier including a first high pass filter;
    a pulse shaping amplifier card, to condition the signal received from the pre-amplifier; and
    a multi-channel analyser.

11. An apparatus according to claim 1, further comprising a transport pipe to deliver the pneumatically conveyed particles to the sensor.

12. An apparatus according to claim 1, further comprising an arm to support the acoustic sensor, and the arm is composed of an electrically shielding material.

13. An apparatus according to claim 12, wherein the sensor has an impact face, and the arm enables the impact face of the acoustic sensor to be arranged at a predetermined angle to the flow of the pneumatically conveyed particles.

14. A method for measuring the size of particles in pneumatic flows, comprising:
    monitoring acoustic signals produced by collisions of the pneumatically conveyed particles with a sensor;
    determining, in respect of each impact, the peak height of the acoustic signal;
    determining a peak height distribution from a series of acoustic signals,
    calculating the particle size according to Hertzian Impact Theory; and
    compensating for sensor wear by measuring acoustic signal overshoot for each pulse.

15. A method according to claim 14, comprising determining a signal duration distribution from the series of acoustic signals.

16. A method according to claim 14, comprising measuring the flow velocity of the pneumatic stream.

17. A method according to claim 14, wherein the density of the particles is known.

* * * * *

UNITED STATES PATENT AND TRADEMARK OFFICE
CERTIFICATE OF CORRECTION

PATENT NO. : 7,213,475 B2
APPLICATION NO. : 10/312327
DATED : May 8, 2007
INVENTOR(S) : Peter John Coghill It is certified that error appears in the above-identified patent and that said Letters Patent is hereby corrected as shown below:

Title Page:

Please amend as follows:

(73) Assignee: Delete "Common Wealth" and insert therefor --Commonwealth-- and delete "Campbel" and insert therefor --Campbell--.

Signed and Sealed this

Eighth Day of April, 2008

JON W. DUDAS
*Director of the United States Patent and Trademark Office*